(12) United States Patent
Cho (10) Patent No.: US 7,282,037 B2
(45) Date of Patent: Oct. 16, 2007

(54) SKIN CARE APPLIANCE

(75) Inventor: Hee-Yoon Cho, Seoul (KR)

(73) Assignee: Doctors Tech Co., Ltd., Seoul (KR)

( * ) Notice: Subject to any disclaimer, the term of this patent is extended or adjusted under 35 U.S.C. 154(b) by 482 days.

(21) Appl. No.: 10/870,176

(22) Filed: Jun. 16, 2004

(65) Prior Publication Data

US 2004/0260212 A1 Dec. 23, 2004

(30) Foreign Application Priority Data

Jun. 17, 2003 (KR) .................. 10-2003-0039232
Jun. 17, 2003 (KR) .............. 20-2003-0019103 U
Apr. 8, 2004 (KR) .................. 10-2004-0024029

(51) Int. Cl.
*A61H 1/00* (2006.01)
*A61H 1/02* (2006.01)
*A61H 5/00* (2006.01)

(52) U.S. Cl. ................. 601/80; 601/46; 601/72; 601/15; 601/17; 601/21

(58) Field of Classification Search ............ 601/46, 601/48, 72, 73, 80, 15, 17, 21; 607/145, 607/88–91, 80, 93, 81–86
See application file for complete search history.

(56) References Cited

U.S. PATENT DOCUMENTS 2,413,879 A * 1/1947 Marty .................. 601/18
4,364,378 A * 12/1982 Seuss et al. ............ 601/21
4,708,127 A * 11/1987 Abdelghani .............. 601/2
5,471,695 A * 12/1995 Aiyar .................... 15/22.1
5,792,080 A * 8/1998 Ookawa et al. ......... 601/115
6,375,630 B1 * 4/2002 Cutler et al. ............ 601/57

FOREIGN PATENT DOCUMENTS

JP 404309100 A * 10/1992

* cited by examiner

*Primary Examiner*—Justine R. Yu
*Assistant Examiner*—Kristen Matter
(74) *Attorney, Agent, or Firm*—Jeffer Mangels Butler & Marmaro LLP (57) ABSTRACT

Disclosed is a skin care appliance capable of realizing various skin care modes using an oscillator vibrating up and down in the way of a magnetic coil, conducting the galvanic massage and the iontophoresis massage based on the oscillator, and making the magnetic-color-sound therapy. The skin care appliance includes a case with a predetermined shape, and a vibration unit installed within the case and having an oscillator. The oscillator oscillates in the way of a magnetic coil upon receipt of the power from a power supply unit. An outer electrode is charged to a polarity opposite to the polarity of the oscillator, and placed at the case. A switch unit is provided at the case. A control unit controls the vibration unit in accordance with the signals from the switch unit. The oscillator includes a housing, a magnet assembly fixed to the bottom end of the housing to generate magnetism, a bobbin wound with a coil for generating the up and down vibrations in relation to the magnet assembly in the way of a magnetic coil, at least one damper installed within the housing to support the bobbin, and a vibrator combined with the bobbin to make the vibration together.

16 Claims, 8 Drawing Sheets

SKIN CARE APPLIANCE

BACKGROUND OF THE INVENTION (a) Field of the Invention

The present invention relates to a skin care appliance, and in particular, to a compact skin care appliance which realizes various skin care modes using a vibrator vibrating up and down in a way of a magnetic coil, and makes the galvanic and iontophoresis massages as well as the magnetic-color-sound (M-C-S) therapy.

(b) Description of Related Art

In order to make excellent skin care effect, Korean Patent No. 319493 discloses a skin care appliance using ultraviolet and far-infrared rays together with a vibrator. The vibrator has a vibration motor to realize the cleansing, massage and lifting modes.

However, with the skin care appliance, as the rotational movement of the vibration motor is shifted into the rectilinear or cam movement to stimulate the target skin, noise is much generated during the power transmission of the vibration motor, and this is liable to give unpleasant sensation to the user. As most of the skin stimulation force is horizontally diffused parallel to the skin, the force exerted vertical to the skin is reduced, and the desired skin massage effect cannot be obtained.

Furthermore, the skin care appliance is extremely restricted in its usage mode and function, and some problem is made in performing the skin care operation effectively.

SUMMARY OF THE INVENTION

It is an object of the present invention to provide a skin care appliance which has a vibrator vibrating up and down in a way of a magnetic coil.

It is another object of the present invention to provide a skin care appliance capable of realizing various modes, such as a cleansing mode, an eye zone mode, a facial mode, a lifting mode, and a vitamin mode.

It is still another object of the present invention to provide a skin care appliance capable of conducting the galvanic and iontophoresis massages while realizing the above modes.

It is still another object of the present invention to provide a skin care appliance capable of making the magnetic-color-sound (M-C-S) therapy while realizing the above modes.

These and other objects may be achieved by a skin care appliance with the following features.

The skin care appliance includes a case with a predetermined shape, and a vibration unit installed within the case and having an oscillator. The oscillator oscillates in the way of a magnetic coil upon receipt of the power from a power supply unit. An outer electrode is charged to a polarity opposite to the polarity of the oscillator and placed at the case. A switch unit is provided at the case. A control unit controls the vibration unit in accordance with the signals from the switch unit.

The vibration unit has a housing, a magnet assembly fixed to the bottom end of the housing to generate magnetism, a bobbin wound with a coil for generating the up and down vibrations in relation to the magnet assembly in a way of a magnetic coil, one or more dampers installed within the housing to support the bobbin, and the oscillator combined with the bobbin to make the vibration together.

The dampers have a first damper mounted at a first seat of the housing over the bobbin, and a second damper mounted at a second seat of the housing over the first damper. A third damper for sealing may be further mounted over the second damper.

A bobbin penetrates the first damper, and the oscillator is screw-coupled to the second damper.

The second damper has an outer ring with an electrode terminal, an inner ring placed inside of the outer ring, a plurality of connection pieces placed between the inner and the outer rings to interconnect the rings in the shape of "⊃," a plurality of support pieces proceeding from the ends of the connection pieces to the center of the inner ring and connected to each other, and a screw insertion hole formed at the center of the inner ring and surrounded by the interconnected portion of the support pieces.

A screw coupling hole is internally formed at the oscillator while facing the screw insertion hole, and three insertion pieces are provided at the bottom end of the oscillator such that the pieces are inserted between the support piece neighbors of the second damper.

While the insertion pieces are inserted between the support piece neighbors, the oscillator is combined with the second damper in a body by a screw coupled to the screw coupling hole through the screw insertion hole.

One of the supports pieces has a width greater than that of the other support pieces such that the combination of the second damper with the oscillator is made while maintaining the directionality.

The second damper combined with the oscillator is preferably formed with stainless steel such that it can well endure under the repeated vibrations of the oscillator.

The oscillator has a plastic body, and a coating film formed on the front end of the plastic body with platinum metals, such as rhodium, nickel and platinum.

It is particularly preferable to select rhodium among the platinum metals because it does not induce any harmful effect, such as allergy, even to the sensitive skin.

The coating film formed on the body of the oscillator reinforces the electrical communication passage by the screw coupling the second damper to the oscillator so that the power applied through the electrode terminal is well transmitted to the oscillator.

The electrical communication between the second damper and the oscillator enables the iontophoresis massage by charging the oscillator either positively or negatively with the current applied through the electrode terminal of the second damper. An outer electrode is provided at the knob of the case.

The outer electrode has a plastic body and a conductive coating film formed on the plastic body with a conductive material, and is screw-coupled to a printed circuit board (PCB) with the control unit to make the electrical communication.

Consequently, a closed circuit is constructed with the sequential flow of the second damper, the oscillator, the human body and the outer electrode, thereby enabling the iontophoresis.

The magnet assembly fixed to the bottom end of the housing has a permanent magnet, an upper core member having a through hole at its center and mounting the permanent magnet at its outer circumference, and a lower core member having a protrusion inserted into the through hole and combined with the upper core member to fix the permanent magnet.

A predetermined gap is made between the inner circumference of the through hole and the outer circumference of the protrusion. The coil wound on the bobbin is inserted into the gap. With the application of the power, the bobbin is vibrated up and down in the way of a magnetic coil, and the oscillator and the second damper combined with the bobbin are oscillated up and down.

The switch unit has a power button, a mode selection button, and a level selection button.

A cleansing mode, an eye zone mode, a facial mode, a lifting mode and a vitamin mode are selected by the mode selection button.

For instance, with the turning on of the power button, when the mode selection button is operated one to five times, the cleansing mode to the vitamin mode may be realized in a stepped manner.

It is preferable in effectively caring the skin to realize the above five modes in a stepped manner.

A low level, a medium level, a high level and a non-vibration level are selected by the level selection button.

The skin care appliance may make magnetic, color and sound therapies.

A cover is fixed to the case. In order to make the magnetic therapy, an ND (Nd—Fe—B) magnet radiating the highest magnetic energy among the rare earth magnets is internally fitted to the cover. The blood circulation of the skin is facilitated due to the magnetic field from the ND magnet.

The ND magnet may be operated to detachably fix the cover to the case. For this purpose, a magnet fixation plate may be provided at front end of the case. In this case, the magnet fixation plate may function as a damper to guide the up and down movements of the oscillator.

Meanwhile, a light emission unit is provided at the case to emit light with a predetermined wavelength, and make a color therapy.

The light emission unit has red-colored light sources expressing the skin activation effect, and blue-colored light sources expressing the skin appeasement effect. Of course, the light emission unit may have light sources irradiating ultraviolet, infrared or visible rays.

A voice output unit is installed within the case with a voice IC mounted on a PCB with the control unit, and an amplifier for amplifying the signals from the voice IC. The voice messages to be output to the user in accordance with the signals of the mode selection switch are memorized at the voice IC.

When the signals from the voice IC are amplified at the amplifier, and transmitted to the vibration unit, the bobbin of the vibration unit is vibrated in the way of a magnetic coil so that the dampers are operated as a soundboard to thereby output a predetermined voice message. Of course, the voice output unit may further include a speaker.

In order to make the sound therapy, an outer input terminal is provided at the case, and connected to a sound player, such as MP3.

With the sound therapy, the sound input from the outside, such as music, acoustic sound and sound source, is inverted into vibration energy, and the oscillator is oscillated in accordance with the sound frequency such that the user can hear the sound through the bone vibration or air vibration.

Of course, it is possible to alter the range of vibration frequency and width used at the respective modes as well as the mode realization time by varying the relevant program via the outer input terminal.

BRIEF DESCRIPTION OF THE DRAWINGS

The above and other advantages of the present invention will become more apparent by describing preferred embodiments thereof in detail with reference to the accompanying drawings in which.

DETAILED DESCRIPTION OF PREFERRED EMBODIMENTS

The present invention will be described more fully hereinafter with reference to the accompanying drawings, in which preferred embodiments of the invention are shown.

Figure 1:
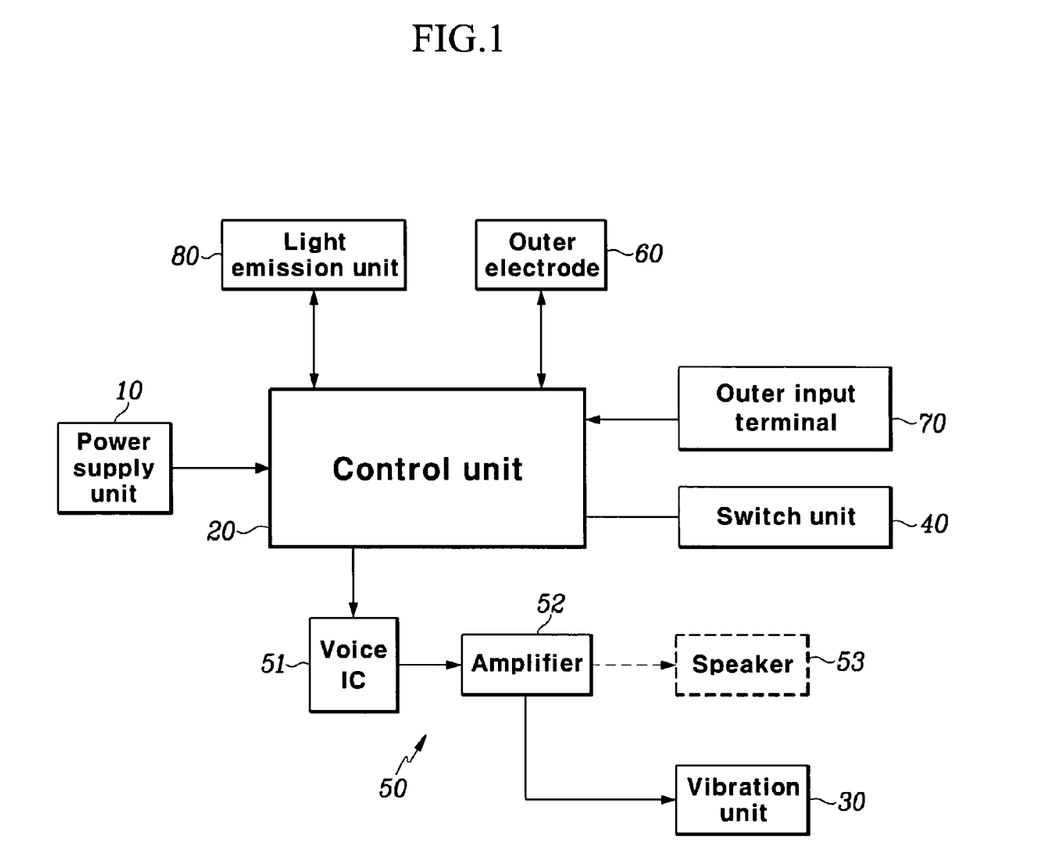
FIG. 1 is a block diagram schematically illustrating a skin care appliance according to an embodiment of the present invention.
Figure 2:
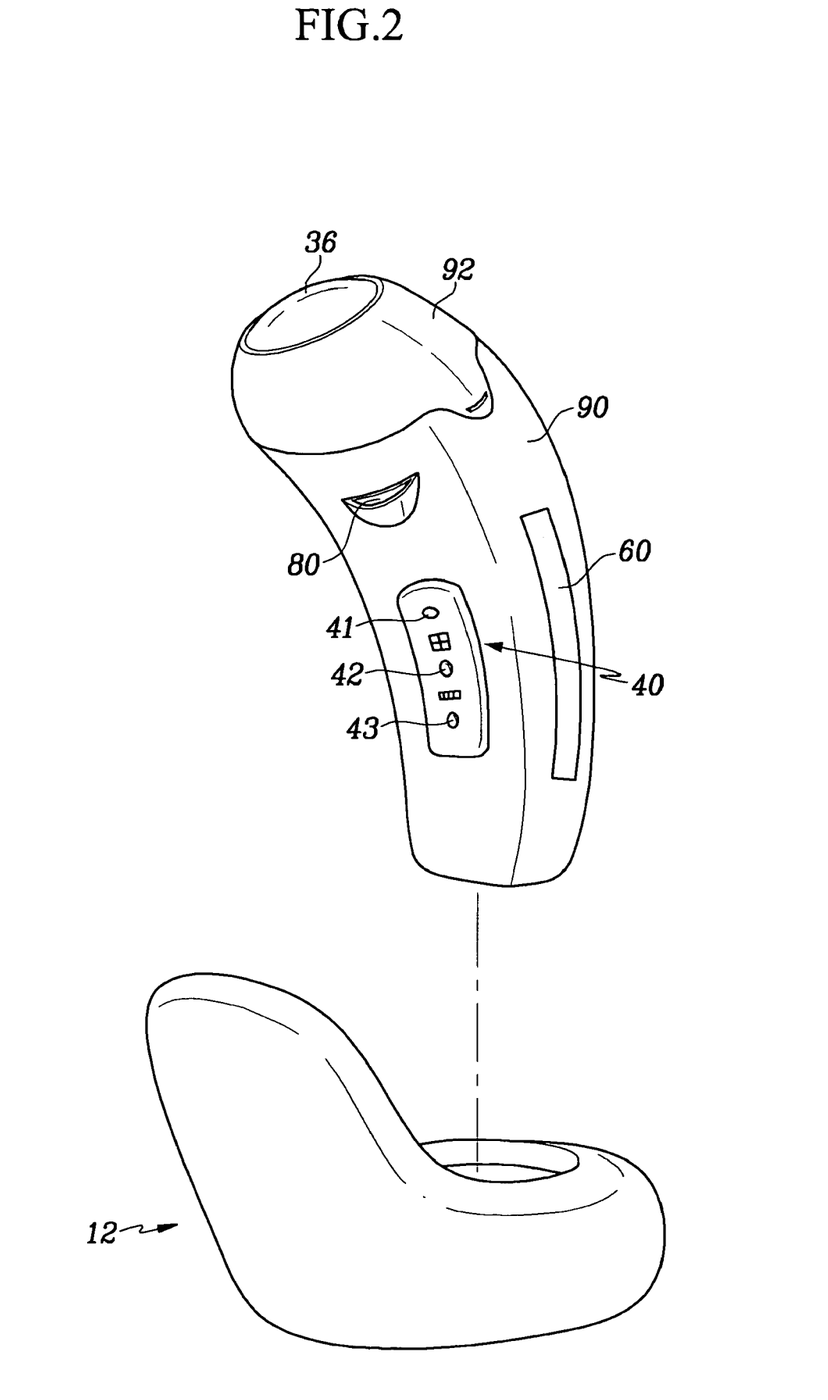
FIG. 2 is a perspective view of the skin care appliance with a case according to the embodiment of the present invention, schematically illustrating the apparent structure thereof.
Figure 3:
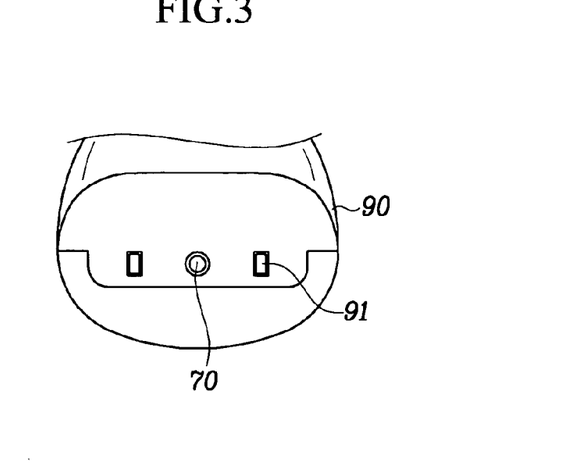
FIG. 3 is a bottom view of the case shown in FIG. 2.
Figure 4:
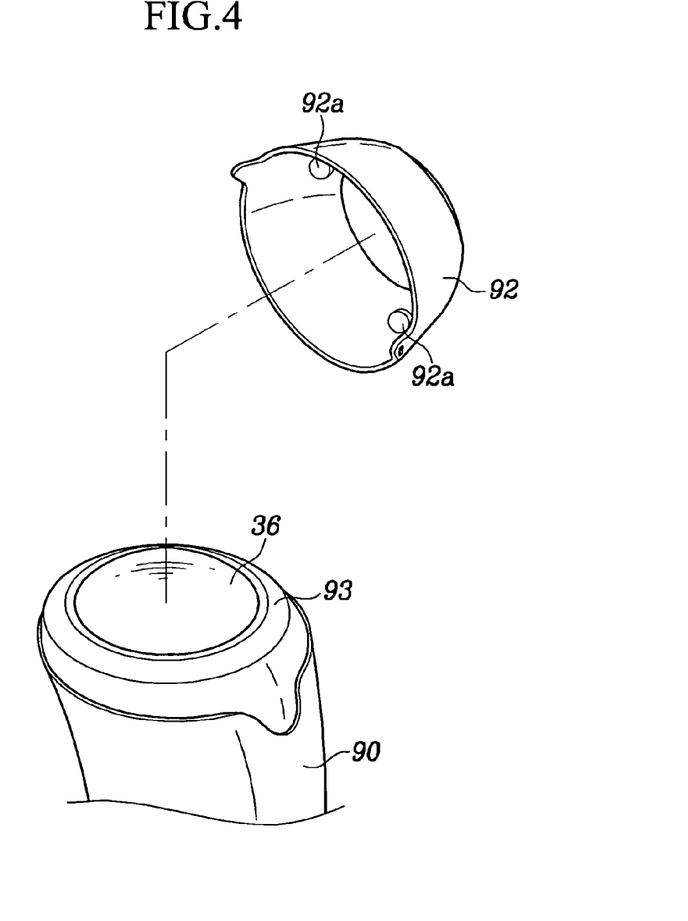
FIG. 4 is a partial perspective view of the case shown in FIG. 2 with the separation of a cover.

FIG. 1 is a block diagram schematically illustrating a skin care appliance according to an embodiment of the present invention, and FIG. 2 is a perspective view of the skin care appliance with a case according to the embodiment of the present invention, schematically illustrating the apparent structure thereof. FIG. 3 is a bottom view of the case shown in FIG. 2, and FIG. 4 is a partial perspective view of the case shown in FIG. 2 with the separation of a cover.

Figure 5:
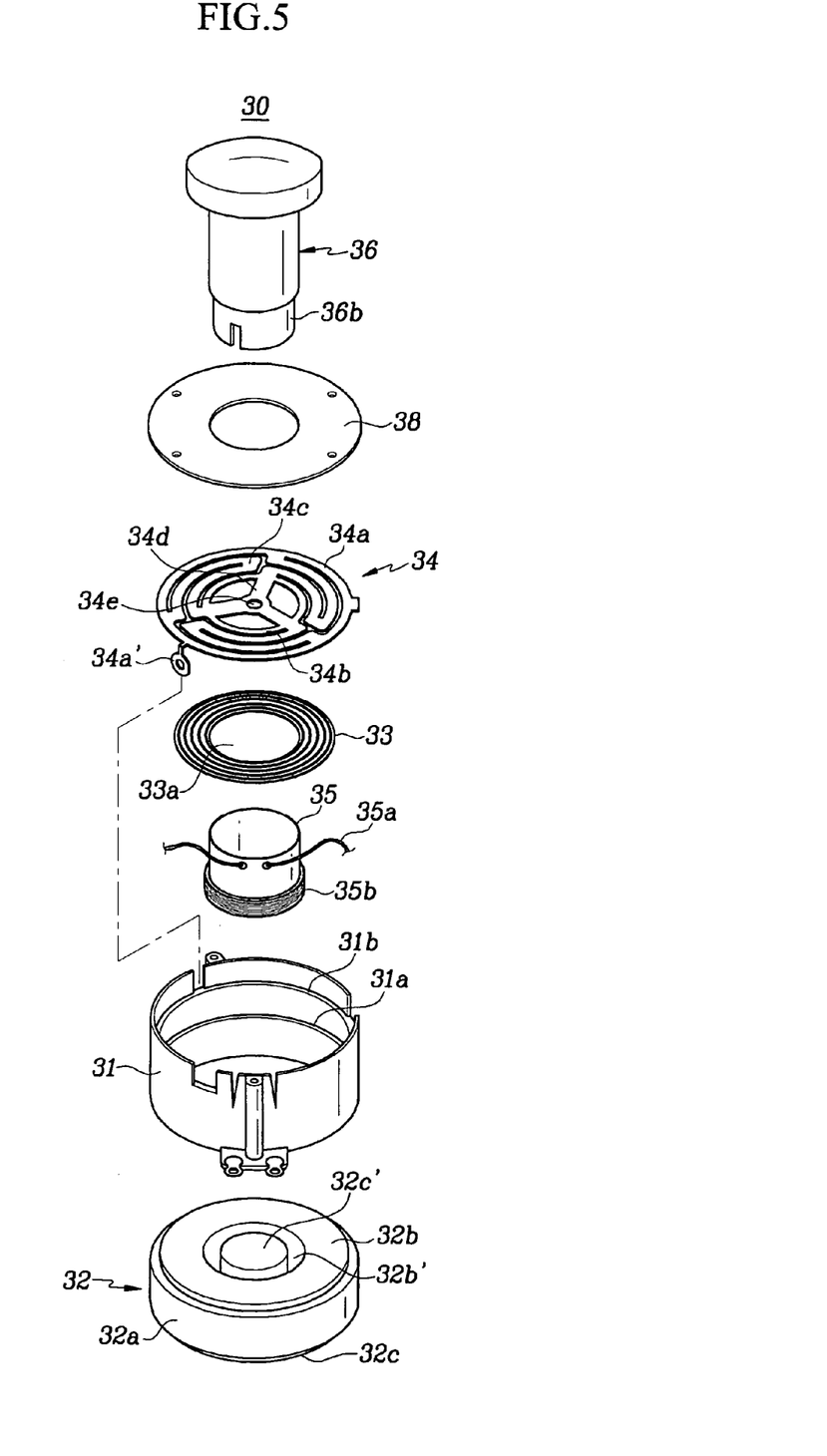
FIG. 5 is an exploded perspective view of a vibration unit of the skin care appliance shown in FIG. 1.
Figure 6:
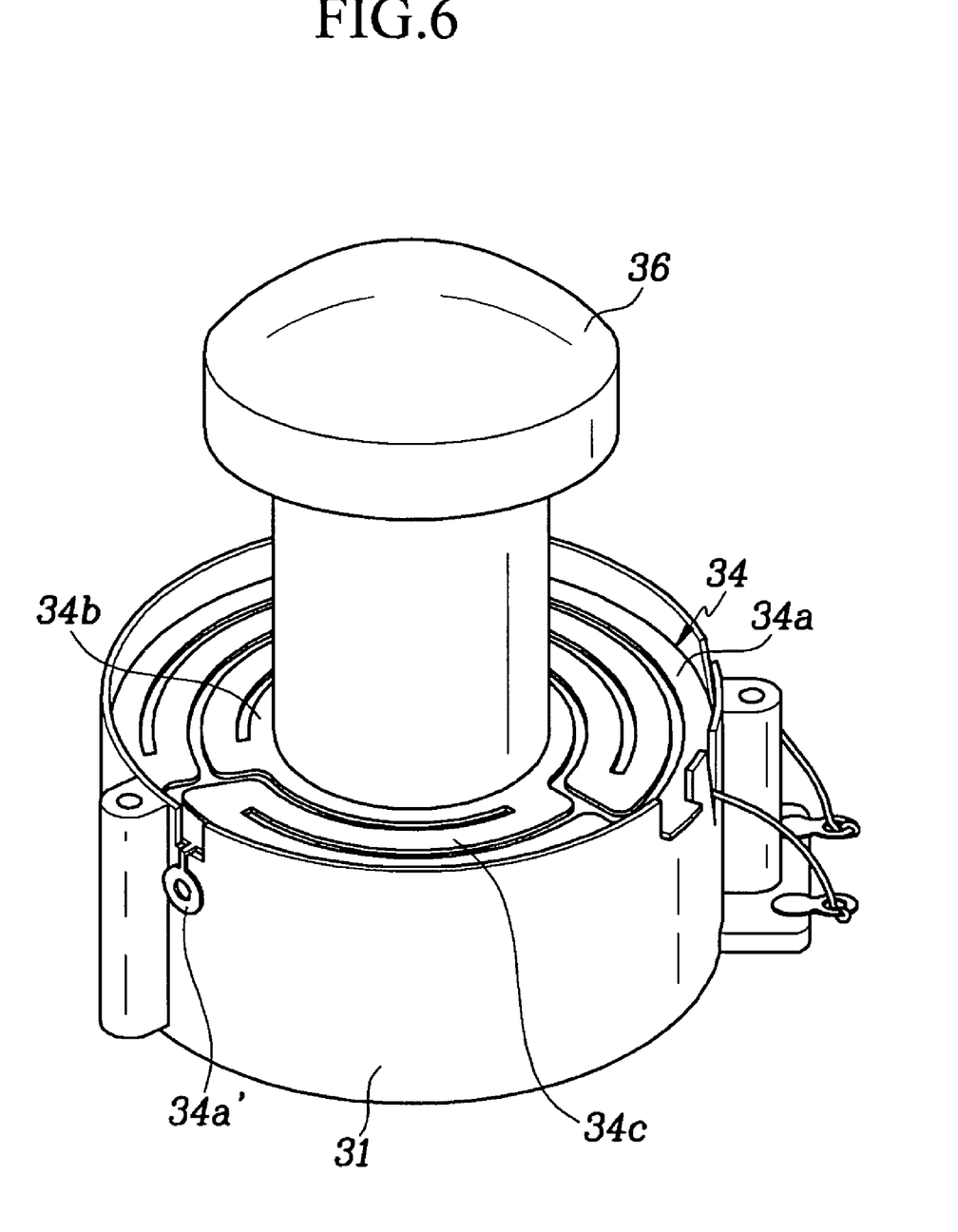
FIG. 6 is a perspective view of the vibration unit shown in FIG. 5, illustrating the combinatorial state thereof.
Figure 7:
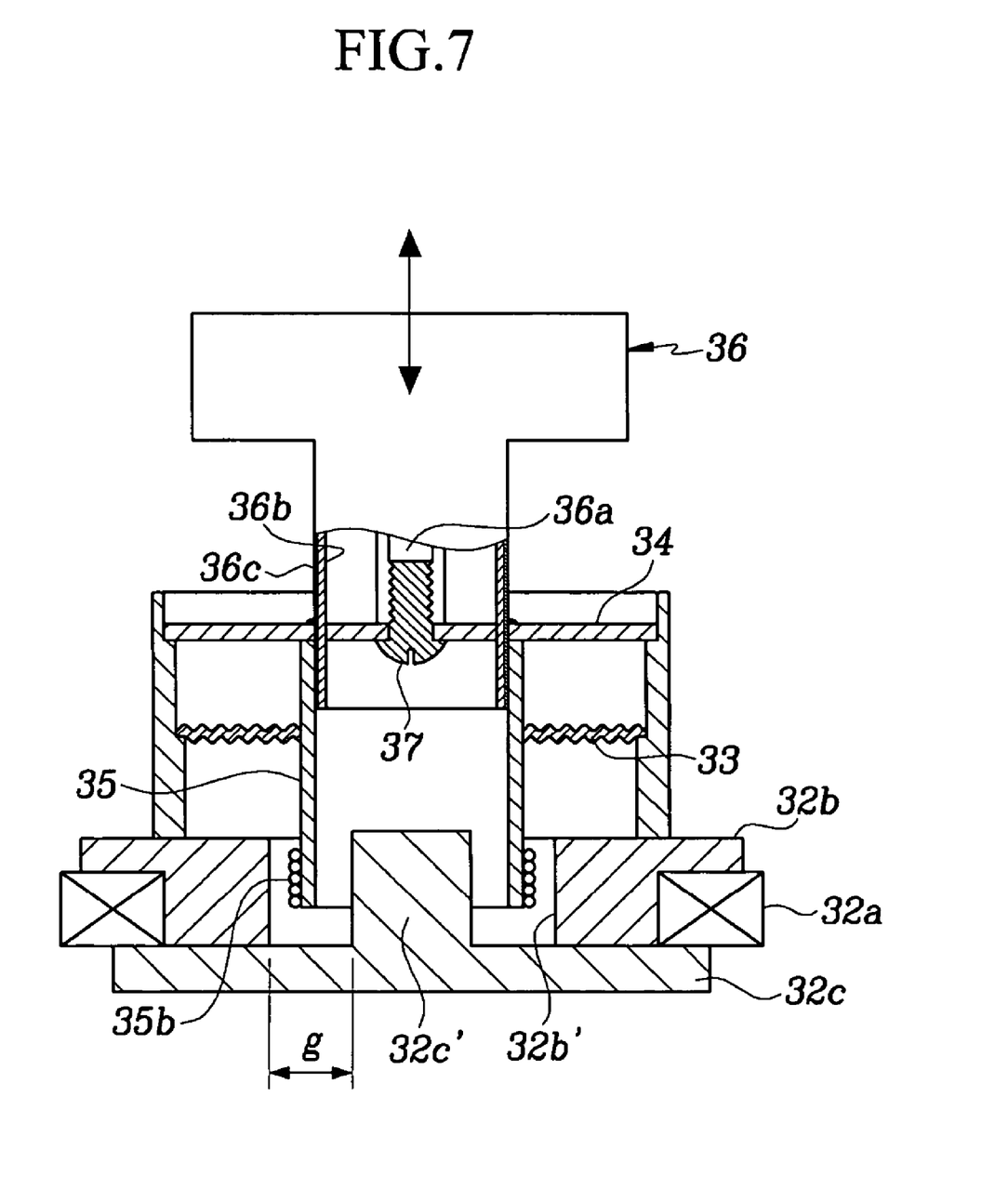
FIG. 7 is a cross sectional view of the vibration unit shown in FIG. 6, taken in the horizontal direction.

FIG. 5 is an exploded perspective view of a vibration unit of the skin care appliance shown in FIG. 1, and FIG. 6 is a perspective view of the vibration unit shown in FIG. 5, illustrating the combinatorial state thereof. FIG. 7 is a cross sectional view of the vibration unit shown in FIG. 6, taken in the horizontal direction. FIGS. 8A to 8D are diagrams of current waveforms made when a cleansing mode, an eye zone mode, a facial mode, a lifting mode and a vitamin mode are realized using the skin care appliance according to the embodiment of the present invention.

As shown in the drawings, the skin care appliance includes a power supply unit 10, a control unit 20, a vibration unit 30, a switch unit 40, a voice output unit 50, an outer electrode 60, an outer input terminal 70, and a light emission unit 80.

The power supply unit 10 applies the driving power to the relevant parts of the skin care appliance. The power supply unit 10 includes a secondary battery (not shown) to be recharged using a placed charger 12.

The control unit 20 controls the vibration unit 30, the voice output unit 50 and the light emission unit 80 in accordance with the signals of the switch unit 40. Furthermore, the control unit 20 controls the vibration unit 30 in accordance with the sounds input from the outer input terminal 70.

As shown in FIGS. 5 to 7, the vibration unit 30 according to the embodiment of the present invention includes a housing 31, a magnet assembly 32, first and second dampers 33 and 34, a bobbin 35, and an oscillator 36.

The housing 31 is cylinder-shaped with opened top and bottom ends, and internally provided with first and second seats 31a and 31b mounting the first and the second dampers 33 and 34 thereon.

The magnet assembly 32 is fixed to the bottom end of the housing 31 to create magnetism. In this embodiment, the magnet assembly 32 has a permanent magnet 32a, an upper core member 32b having a through hole 32b' at its center and mounting the permanent magnet 32a at its outer circumference, and a lower core member 32c having a protrusion 32c' inserted into the through hole 32b' and combined with the upper core member 32b to fix the permanent magnet 32a. A predetermined gap is made between the inner circumference of the through hole 32b' and the outer circumference of the protrusion 32c'.

When the second damper 34 is vibrated, the first damper 33 mounted at the first seat 31a of the housing 31 over the magnet assembly 32 prevents the second damper 34 from colliding against the magnet assembly 32.

The first damper 33 is formed with a circular ring having a bobbin insertion hole 33a at its center, and fixed to the housing 31 by an adhesive, such as epoxy resin, while being mounted at the first seat 31a.

A bobbin 35 is inserted into the bobbin insertion hole 33a of the first damper 33. A coil 35b is provided at the bobbin 35 to receive the power via an electric wire 35a. The coil 35b is inserted into the gap of the magnet assembly 32. When the power is applied to the coil 35b, the bobbin 35 is vibrated up and down as indicated by the arrow of FIG. 7, due to the magnetic coil phenomenon occurred between the coil 35b and the permanent magnet 32a. At this time, the first damper 33 guides the up and down vibrations of the bobbin 35.

The second damper 34 placed over the first damper 33 includes an outer ring 34a with an electrode terminal 34a', an inner ring 34b placed inside of the outer ring 34a, and three connection pieces 34c placed between the inner ring 34b and the outer ring 34a to interconnect them in the shape of "⊃". The second damper 34 further has three support pieces 34d proceeding from the ends of the connection pieces 34c to the center of the inner ring 34b and connected to each other, and a screw insertion hole 34e formed at the center of the inner ring 34b and surrounded by the interconnected portion of the support pieces 34d.

The three support pieces 34d are angled against each other by 120°. One of the support pieces 34d preferably has a width greater than that of the other support pieces. This makes it easy to maintain the directionality when the second damper 34 is combined with the oscillator 36 to be described later.

The second damper 34 is preferably formed with a stainless steel having a thickness of 0.25 mm such that it has a reasonable endurance under the repeated vibrations of the oscillator 36. The second damper 34 is adhered to the housing 31 by an adhesive, such as epoxy resin, while being mounted at the second seat 31b.

Meanwhile, a screw coupling hole 36a is formed at the oscillator 36 while facing the screw insertion hole 34e, and three insertion pieces 36b are provided at the bottom end of the oscillator 36 such that they are inserted between the support piece neighbors 34d of the second damper 34.

The oscillator 36 is combined with the second damper 34 in a body by a screw 37 coupled to the screw coupling hole 36a through the screw insertion hole 34e while the insertion pieces 36b being inserted between the support piece neighbors 34d. The insertion pieces 36b of the oscillator 36 are inserted into the bobbin 35 through the top thereof, and internally fitted to the bobbin 35. The oscillator 36 and the second damper 34 are adhered to the bobbin 35 by an adhesive, such as epoxy resin, and oscillated when the bobbin 35 vibrates up and down.

The reference numeral 38 of FIG. 5 indicates a third damper for sealing, which is formed with silicon.

Meanwhile, the oscillator 36 is preferably structured such that a coating film 36c is formed on the surface of a plastic body 36b with platinum metals, such as rhodium Rh, nickel Ni and platinum Pt. It is particularly preferable to select rhodium among the platinum metals because it does not induce any harmful effect, such as allergy, even to the sensitive skin.

Of course, it is possible to coat the rhodium film only on the front end portion of the oscillator 36 directly contacting the skin. In this case, it is preferable to form a coating film on the oscillator 36 except for the front end portion thereof with metals other than rhodium. The purpose is that the power applied through the electrode terminal 34a' of the second damper 34 is well transmitted to the front end portion of the oscillator 36 via the screw 37 interconnecting the second damper 34 and the oscillator 36, and the coating film 36c.

Consequently, the oscillator 36 is charged either to a positive pole or to a negative pole to thereby make the iontophoresis massage. Furthermore, the polarity of the oscillator 36 is cyclically inverted to thereby make the galvanic massage.

The switch unit 40 is placed at the case 90 with the above-structured vibration unit 30. In this embodiment, the switch unit 40 has a power button 41, a mode selection button 42, and a level selection button 43.

The mode selection button 42 is structured such that a cleansing mode, an eye zone mode, a facial mode, a lifting mode and a vitamin mode can be selected.

The cleansing mode is realized by turning on the power button 41 and operating the mode selection button 42. Similarly, the eye zone mode, the facial mode, the lifting mode and the vitamin mode are realized in a stepped manner by operating the mode selection button 42 once more.

Meanwhile, when the respective modes are realized, the vibration frequency of the oscillator 36 is controlled so that the vibration wave like the α-wave can be generated.

The air usually contains positive and negative ions in a mixture of carbon dioxide, oxygen, nitrogen and hydrogen. The common cleansing based on water or cosmetics removes only the negatively polarized sweat or dust, but not the positively polarized contaminants, such as sebum. Accordingly, with the realization of the cleansing mode, the oscillator 36 is negatively charged to effectively remove the sebum from the skin.

The iontophoresis massage is characterized in that the massage is made while charging the oscillator 36 to any one of the positive and negative polarities. With the cleansing mode, the oscillator 36 is negatively charged using the current waveform shown in FIG. 8A. In the drawing, the horizontal axis indicates the time, and the vertical axis indicates the current polarity.

Figure 8A:
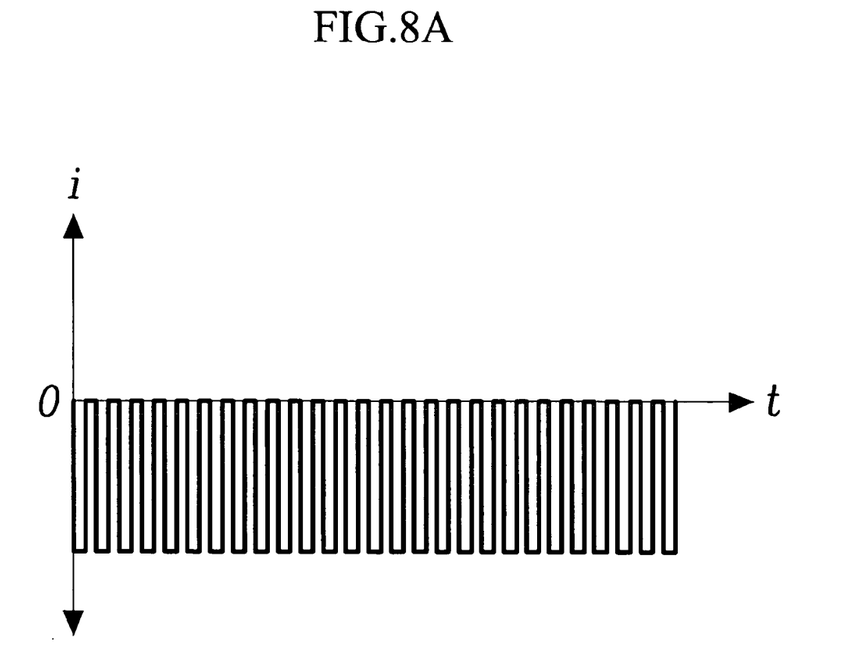
FIGS. 8A to 8D are diagrams of current waveforms made when a cleansing mode, an eye zone mode, a facial mode, a lifting mode and a vitamin mode are realized using the skin care appliance according to the embodiment of the present invention.
Figure 8B:
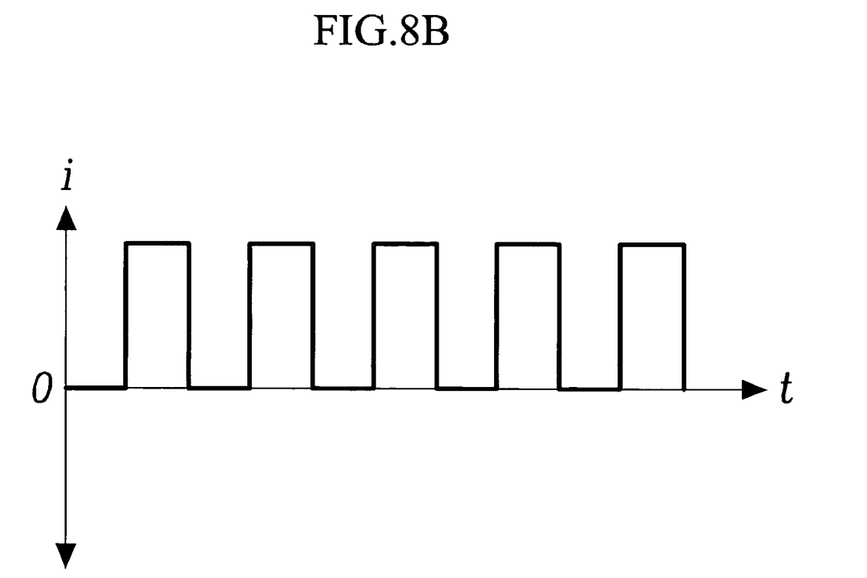
Figure 8C:
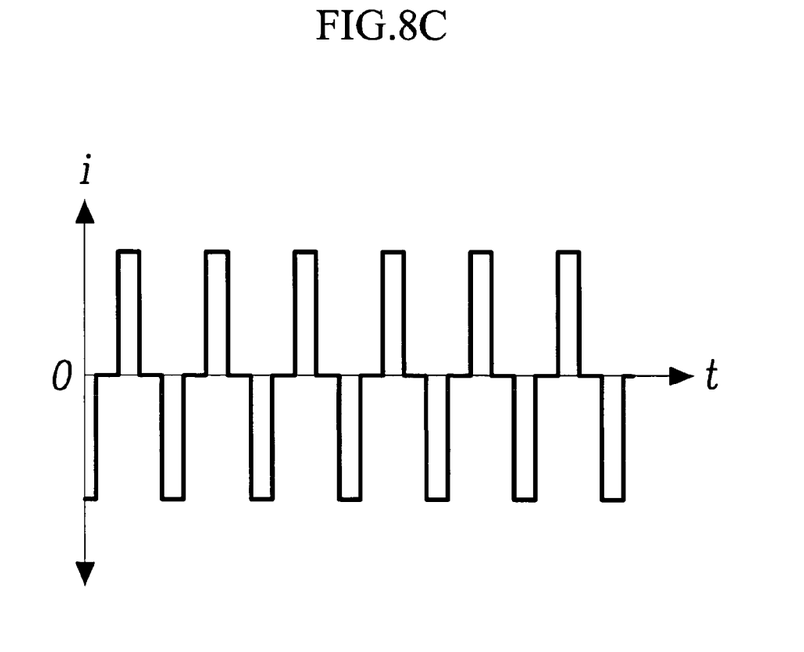

Meanwhile, with the eye zone mode and the facial mode, the oscillator 36 is positively charged using the current waveform shown in FIG. 8B. With the vitamin mode, the oscillator 36 is negatively charged using the current waveform shown in FIG. 8C. Although not specifically explained, the eye zone mode, the facial mode and the vitamin mode all serve to make the iontophoresis massage.

Figure 8D:
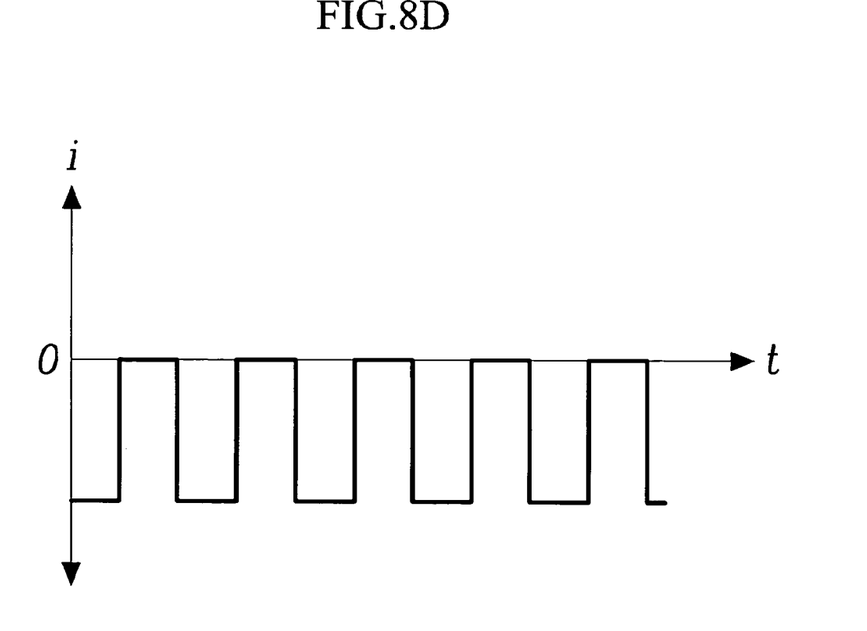

Furthermore, with the lifting mode, the oscillator 36 is cyclically charged to the positive and the negative polarities using the current waveform shown in FIG. 8D. The galvanic massage is characterized in that the massage is made using the positive current and the negative current in a cyclic manner.

With the vitamin mode, ionized vitamin C particles helpful to the skin are injected into the skin. An anti-oxidizing material, such as phosphate, is added to the vitamin C to realize a stable structure.

When the above five modes are realized, the voltage applied to the second damper 34 is controlled to charge the oscillator 36 either positively or negatively. At this time, a closed circuit is constructed through the outer electrode 60 provided at the case of the skin care appliance.

In this embodiment, the outer electrode 60 has a plastic body, and a conductive film coated on the plastic body with a conductive material. The outer electrode 60 is screw-coupled to a PCB with the control unit 20 to make the electrical communication.

Consequently, a closed circuit is constructed with the sequential flow of PCB (not shown), the second damper 34, the oscillator 36, the human body (not shown), the outer electrode 60, and the PCB.

With the realization of the above five modes, the level of the respective modes can be controlled to be low, medium, high and non-vibration by operating the level selection button 43.

Meanwhile, the voice output unit 50 of the skin care appliance includes a voice IC 51 installed on the PCB (not shown) together with the control unit 20, and an amplifier 52 for amplifying the signals from the voice IC 51. The voice messages informing of the modes selected by the mode selection switch to the user are memorized at the voice IC 51.

When the signals from the voice IC 51 are amplified at the amplifier 52, and transmitted to the vibration unit 30, the bobbin 35 of the vibration unit 30 is vibrated in the way of a magnetic coil so that the dampers 33 and 34 are operated as a soundboard to thereby output a predetermined voice message. Of course, the voice output unit 50 may further include a speaker 53.

In addition to the above five operating modes, the skin care appliance according to the embodiment of the present invention may further make a sound therapy, a color therapy, and a magnetic therapy.

With the sound therapy, the sound output from an MP3 and a CD player, such as music, acoustic sound and sound source, is inverted into a vibration energy, and the oscillator 36 is oscillated in accordance with the sound frequency such that the user can hear the sound through the bone vibration or air vibration.

In order to make the sound therapy, as shown in FIG. 4, an outer input terminal 70 is formed at the bottom of the case 90 of the skin care appliance, and a sound cable (not shown) is connected to the terminal 70. A line terminal, a flash memory card connector, a universal serial bus (USB), and a serial high-speed communication port by IEEE1394 (Institute of Electrical and Electronics Engineers) can be used as the outer input terminal 70. The reference numeral 91 of FIG. 4 indicates a charging terminal.

Of course, it is possible to alter the range of vibration frequency and width used at the respective modes as well as the mode realization time by varying the relevant program via the outer input terminal 70.

The sound therapy can be made while realizing the cleansing mode, the eye zone mode, the facial mode, the lifting mode and the vitamin mode at the non-vibration level. Of course, it is evident that the sound therapy might be made even when the above five modes are realized at the levels other than the non-vibration level.

With the color therapy, the light emitted from the light sources differentiated in the wavelength is illuminated onto the skin to care the skin at those wavelengths intrinsic to the respective colors. For this purpose, a light emission unit 80 composed of light sources is provided at the case 90. The light sources may irradiate infrared, ultraviolet, near-ultraviolet or visible rays.

For instance, blue-colored light sources (with wavelengths of 450-500 nm) expressing the skin appeasement effect, and red-colored light sources (with wavelengths of 610-700 nm) expressing the skin activation effect may be used as the light sources.

With the magnetic therapy, the skin caring effect is made due to the magnetic energy during the usage of the skin care appliance.

A magnet 92a is internally attached to the cover 92 detachably fixed to the case 90. The magnet 92a is formed with an ND (Nd—Fe—B) magnet radiating the highest magnetic energy among the rare earth magnets. The blood circulation of the skin is facilitated due to the magnetic field from the magnet 92a.

A magnet fixation plate 93 may be provided at the case 90 such that the cover 92 is detachably fixed to the case 90 using the magnet 92a. Furthermore, a sealing damper 38 is provided at the case 90, and placed under the magnet fixation plate 93.

The magnetic therapy is continuously made during the realization of the five modes. The color therapy may be also made continuously during the usage of the skin care appliance.

As described above, the massage is made using an oscillator vibrating in the way of a magnetic coil so that the noise occurrence is not nearly made compared to the case where the oscillator is oscillated using a motor. Furthermore, as the horizontally diffused force is extremely small so that the massage effect by the oscillator can be improved.

Furthermore, the vibration frequency and width of the oscillator are controlled such that various modes such as a cleansing mode, an eye zone mode, a facial mode, a lifting mode and a vitamin mode can be realized. Furthermore, the iontophoresis massage and the galvanic massage can be selectively made during the realization of those modes.

In addition, the sound therapy based on the outer input terminal, the magnetic therapy based on the MD magnet attached to the cover, and the color therapy based on the light sources can be made, thereby maximizing the massage effect.

Although preferred embodiments of the present invention have been described in detail hereinabove, it should be clearly understood that many variations and/or modifications of the basic inventive concept herein taught which may appear to those skilled in the art will still fall within the spirit and scope of the present invention, as defined in the appended claims.

What is claimed is:

1. A skin care appliance comprising:
   a case with a predetermined shape;
   a vibration unit installed within the case and having an oscillator, the oscillator vibrating in a way of a magnetic coil upon receipt of the power from a power supply unit;
   an outer electrode charged to a polarity opposite to the polarity of the oscillator and placed at the case;
   a switch unit provided at the case; and a control unit for controlling the vibration unit in accordance with the signals from the switch unit,
wherein the vibration unit comprises:
a housing,
a magnet assembly fixed to the bottom end of the housing to generate magnetism,
a bobbin wound with a coil for generating the up and down vibrations in relation to the magnet assembly in a way of a magnetic coil,
one or more dampers installed within the housing to support the bobbin, and
the oscillator combined with the bobbin to make the vibration together,
wherein the dampers comprise:
a first damper mounted at a first seat of the housing over the bobbin, and
a second damper mounted at a second seat of the housing over the first damper, and
wherein the bobbin penetrates the first damper, and the oscillator is screw-coupled to the second damper.

2. The skin care appliance of claim 1 wherein the second damper comprises an outer ring with an electrode terminal, an inner ring placed inside of the outer ring, a plurality of connection pieces placed between the inner and the outer rings to interconnect the rings in the shape of "⊃," a plurality of support pieces proceeding from the ends of the connection pieces to the center of the inner ring and connected to each other, and a screw insertion hole formed at the center of the inner ring and surrounded by the interconnected portion of the support pieces.

3. The skin care appliance of claim 2 wherein the second damper is formed with stainless steel.

4. The skin care appliance of claim 2 wherein a screw coupling hole is internally formed at the oscillator while facing the screw insertion hole, and three insertion pieces are provided at the bottom end of the oscillator such that the pieces are inserted between the support piece neighbors of the second damper.

5. The skin care appliance of claim 4 wherein the oscillator comprises a plastic body, and a coating film formed on the front end of the plastic body with rhodium Rh belonging to the platinum metals.

6. The skin care appliance of claim 5 wherein the electric communication passage between the oscillator and the second damper is made by a screw coupling the oscillator to the second damper, and the coating film.

7. The skin care appliance of claim 1 wherein the outer electrode has a plastic body and a conductive coating film formed on the plastic body with a conductive material, and is screw-coupled to a printed circuit board with the control unit to make the electrical communication.

8. The skin care appliance of claim 1 wherein the switch unit comprises a power button, a mode selection button, and a level selection button.

9. The skin care appliance of claim 8 wherein the mode selection button can select a plurality of modes comprising a cleansing mode, an eye zone mode, a facial mode, a lifting mode and a vitamin mode.

10. The skin care appliance of claim 8 wherein a low level, a medium level, a high level and a non-vibration level are selected by the level selection button.

11. The skin care appliance of claim 1 wherein a magnet fixation plate is provided at the case, and a cover having a magnet for making a magnetic therapy is detachably fixed to the case by the magnet.

12. The skin care appliance of claim 1 wherein a light emission unit is provided at the case to make a color therapy.

13. The skin care appliance of claim 12 wherein the light emission unit comprises a red-colored light source, and a blue-colored light source.

14. The skin care appliance of claim 1 wherein a voice output unit is installed within the case with a voice IC mounted on a printed circuit board with the control unit, and an amplifier for amplifying the signals from the voice IC.

15. The skin care appliance of claim 1 wherein an outer input terminal is provided at the case, and connected to a sound player.

16. The skin care appliance of claim 15 wherein the oscillator is oscillated in accordance with the frequency of the sound input through the outer input terminal.

* * * * *